(12) United States Patent
Hansmann et al.

(10) Patent No.: US 9,933,404 B2
(45) Date of Patent: Apr. 3, 2018

(54) MEASURING DEVICE AND MEASURING METHOD

(71) Applicant: Dräger Safety AG & Co. KGaA, Lübeck (DE)

(72) Inventors: Hans-Ullrich Hansmann, Barnitz (DE); Philipp Rostalski, Lübeck (DE); Andreas Mohrmann, Krummesse (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 14/784,726

(22) PCT Filed: Apr. 15, 2014

(86) PCT No.: PCT/EP2014/001010
§ 371 (c)(1),
(2) Date: Oct. 15, 2015

(87) PCT Pub. No.: WO2014/170017
PCT Pub. Date: Oct. 23, 2014

(65) Prior Publication Data
US 2016/0061800 A1 Mar. 3, 2016

(30) Foreign Application Priority Data
Apr. 16, 2013 (DE) .................. 10 2013 006 543

(51) Int. Cl.
*G01N 33/00* (2006.01)
*G01N 21/78* (2006.01)
*G01N 21/27* (2006.01)

(52) U.S. Cl.
CPC ....... *G01N 33/0073* (2013.01); *G01N 21/783* (2013.01); *G01N 33/0013* (2013.01); *G01N 21/272* (2013.01); *G01N 2201/1241* (2013.01)

(58) Field of Classification Search
CPC ............. G01N 33/0073; G01N 21/783; G01N 33/0013; G01N 21/272; G01N 2201/1241
(Continued)

(56) References Cited

U.S. PATENT DOCUMENTS 3,861,216 A 1/1975 Wachter et al.
4,254,657 A 3/1981 Leichnitz et al.
(Continued)

FOREIGN PATENT DOCUMENTS

DE 15 98 021 A1 3/1970
DE 21 41 496 A1 3/1973
(Continued)

*Primary Examiner* — Brian J Sines
(74) *Attorney, Agent, or Firm* — McGlew and Tuttle, P.C.

(57) ABSTRACT

A measuring device (10) and a measuring method measure a concentration of gaseous and/or aerosol components of a gas mixture. A reaction carrier (14) has a flow channel (42) defining a reaction chamber (46) with an optically detectable reaction material (48) to react with at least one component or with a reaction product of the component. The measuring device (12) includes a gas delivery unit (2) and detection unit (3) having a lighting device (37) for lighting the reaction chamber (46). An optical sensor (38) detects the reaction. An evaluation unit (4) evaluates data of the optical sensor (38) to determines a concentration. The gas delivery unit (2) includes a gas delivering device (28) delivering the gas mixture through the gas outlet channel (18) and a control/regulation unit (31) which controls/regulates a flow of the gas mixture through the flow channel (42) depending on at least one reaction speed parameter.

17 Claims, 11 Drawing Sheets

(58) Field of Classification Search
USPC .......... 422/50, 68.1, 83, 82.05; 436/43, 130
See application file for complete search history.

(56) References Cited

U.S. PATENT DOCUMENTS

| | | |
|---|---|---|
| 5,055,267 A | 10/1991 | Burroughs et al. |
| 5,255,074 A | 10/1993 | Kimbell et al. |
| 5,889,585 A | 3/1999 | Markart |
| 2002/0022932 A1* | 2/2002 | Yamada et al. ................. 702/24 |
| 2003/0049849 A1 | 3/2003 | Mori et al. |
| 2006/0263257 A1 | 11/2006 | Beauchamp et al. |
| 2011/0216953 A1* | 9/2011 | Callahan et al. ............. 382/128 |
| 2012/0063956 A1 | 3/2012 | Truex et al. |

FOREIGN PATENT DOCUMENTS

| | | |
|---|---|---|
| DE | 28 23 315 A1 | 12/1979 |
| DE | 195 38 125 A1 | 4/1997 |
| DE | 198 25 103 A1 | 12/1998 |
| DE | 10 2004 027 130 A1 | 1/2005 |
| DE | 10 2004 027 132 A1 | 1/2005 |
| EP | 1 643 238 A1 | 4/2006 |
| JP | 2003 270236 A | 9/2003 |
| JP | 2011 002400 A | 1/2011 |

\* cited by examiner

MEASURING DEVICE AND MEASURING METHOD

CROSS REFERENCE TO RELATED APPLICATIONS

This application is a United States National Phase Application of International Application PCT/EP2014/001010 filed Apr. 15, 2014 and claims the benefit of priority under 35 U.S.C. § 119 of German Patent Application 10 2013 006 543.7 filed Apr. 16, 2013 the entire contents of which are incorporated herein by reference.

FIELD OF THE INVENTION

The present invention pertains to a measuring system and a measuring device for measuring a concentration of gaseous and/or aerosol components of a gas mixture for a reaction carrier, which has at least two flow channels, wherein at least one flow channel forms a reaction chamber with a reactant and the reactant reacts with at least one of the components to be measured in the gas mixture in an optically detectable manner. The present invention pertains, furthermore, to a reaction carrier for such a measuring device as well as to a measuring method for measuring a concentration of gaseous and/or aerosol components of a gas mixture.

BACKGROUND OF THE INVENTION

Gas detector tubes, which are filled with a reactant, which reacts with a chemical compound to be determined in an optically detectable reaction, are known from the state of the art. For example, a defined quantity of a gas mixture is pumped with a hand pump through the gas detector tube. A concentration of the chemical compound to be measured is subsequently determined by means of a discoloration of the reactant.

Moreover, so-called chip-based measuring systems are known, in which the reactant is provided in a plurality of reaction chambers, which are arranged on a reaction carrier and can be used for a measurement each. The reaction carrier can be inserted into a measuring device, which detects the reaction carrier and carries out a corresponding measuring method for measuring a concentration of the corresponding component of the gas mixture.

The measuring time with such a measuring system may be rather long, for example, several minutes, depending on the type of the chemical compound to be measured and the concentration range to be measured.

SUMMARY OF THE INVENTION

An object of the present invention is to provide an improved measuring device as well as an improved measuring method, which makes possible an increased flexibility in the measuring method and fast output of the measurement results.

A measuring device according to the present invention for measuring a concentration of gaseous and/or aerosol components of a gas mixture is designed for a reaction carrier that has at least one flow channel, wherein the flow channel forms a reaction chamber with a reactant, which is designed to react with at least one component to be measured in the gas mixture or with a reaction product of the component to be measured in an optically detectable manner. The measuring device comprises a gas delivery unit with a gas delivery device for delivering the gas mixture through the gas outlet channel, and a detection unit with a lighting device for illuminating the reaction chamber of the reaction carrier, with an optical sensor for detecting the optically detectable reaction, and an analysis unit for analyzing the data detected by the optical sensor of the optically detectable reaction and for determining a concentration of the component of the gas mixture. The gas delivery unit has, furthermore, a control/regulation unit, which is designed (configured) to control or regulate a flow of the gas mixture through the flow channel as a function of at least one reaction rate parameter.

This makes it possible to adapt a flow rate of the gas mixture, as a result of which the measuring method can be varied in a flexible manner, in order to achieve, for example, shorter measuring times or lower measuring inaccuracies. In addition, a wider concentration range can be measured due to the dynamic adaptation of the flow of the gas mixture through the flow channel, because, for example, a reaction that takes place too rapidly at high concentrations can be slowed down by reducing the flow of the gas mixture. The reaction range, which corresponds to the length of the reaction chamber in the direction of flow, can, moreover, be optimally utilized, and utilization of the entire reaction range makes possible an optimal measurement result, on the one hand, or, on the other hand, a plurality of measurements can be performed on one reaction chamber by utilizing partial areas. It is also possible, as an alternative, to adapt the flow such that preset measuring times are always obtained for certain measurements. Fluctuations of the mass flow during the measurement can be compensated, as a result of which the accuracy of the concentration determination is increased.

For example, the speed of the reaction front propagating in the direction of flow in the reaction chamber may be a reaction rate parameter, and the control/regulation unit of the gas delivery unit is designed (configured) to control or regulate the flow of the gas mixture through the flow channel as a function of the speed of the reaction front.

The flow rate, for example, the mass flow or volume flow, can be adapted in this way in order to obtain an optimal speed of the reaction front, as a result of which the duration of the measurement, on the one hand, and the accuracy of the measurement, on the other, can be affected. Regulation of the reaction front is preferably made possible.

A reaction rate parameter may also be a temperature of the gas mixture flowing through the reaction chamber, the detection unit being designed (configured) to determine the temperature of the gas mixture, and the control/regulation unit of the gas delivery unit is designed to control or regulate the flow of the gas mixture through the flow channel as function of the temperature of the gas mixture.

The course of the measuring method can be adapted in this way to the temperature of the gas mixture and an optimal measurement can be made possible at different temperatures. To determine the temperature, the temperature can be measured directly in the flow channel of the reaction carrier by a corresponding temperature-measuring element, or the temperature of the reaction carrier and/or of the measuring device is measured by corresponding temperature-measuring elements. A course over time of the temperature of the gas mixture is preferably measured or calculated during the measurement.

The detection unit may be designed to detect the speed of the reaction front propagating in the direction of flow in the reaction chamber and to determine a preliminary concentration from the speed of the reaction front.

A preliminary concentration can already be determined at an early stage of the measurement by detecting the speed of the reaction front. The user can be warned in this way in time, even if a desired accuracy of the measurement cannot yet be reached. This is especially advantageous in case of chemicals that are hazardous for health, because, for example, corresponding protective measures can thus be taken more rapidly. Furthermore, the speed of the reaction front can be detected continuously in the course of the measurement by taking, for example, variable mass flows of the gas mixture into account during the measurement.

The use of an optical sensor with high spatial resolution, for example, of a digital camera, can make high accuracy possible in detecting the position of the reaction front and hence an improved detection of the speed of the reaction front.

For example, the lighting device is designed to illuminate the reaction chamber with a broad-band spectrum, which comprises especially white light and/or infrared spectral ranges.

A plurality of different optically detectable reactions between reactants and a plurality of chemicals, which are in the broad spectral range, are available due to the use of a broad spectral range.

The optical sensor is preferably a multichannel sensor, which can detect a plurality of color channels, and the analysis unit is designed to perform a weighting of the color channels during the analysis of the data of the optical sensor.

This makes possible, on the one hand, the use of the plurality of different optically detectable reactions and, on the other hand, an optimized analysis of the respective optically detectable reaction selected in the selected reaction chamber by a correspondingly selected weighting of the color channels.

The detection unit may be designed to detect an intensity gradient of a reaction front propagating in the direction of flow in the reaction chamber, and the analysis unit may be designed to determine the concentration of the component of the gas mixture exclusively from optically detectable parameters, especially the reaction front and/or a temperature-measuring element for determining a temperature.

Thus, no additional sensors are necessary besides the optical sensor for determining the concentration, and the mode of construction of the measuring device is simplified and thus more cost-effective.

A measuring method according to the present invention is provided for measuring a concentration of gaseous and/or aerosol components of a gas mixture with a reaction carrier, which has at least one flow channel, which forms a reaction chamber with a reactant, which is designed to react with at least one component to be measured in the gas mixture or with a reaction product of the component to be measured in an optically detectable manner, and with a measuring device, which comprises a gas delivery unit and a detection unit. The measuring method comprises the method steps of illuminating the reaction chamber of the reaction carrier; of delivering a gas mixture through the flow channel at a flow rate; of detecting a reaction rate parameter during the delivery of the gas mixture; of controlling or regulating the flow rate as a function of at least one reaction rate parameter; and of determining and outputting a measurement result of the concentration of the component to be measured in the gas mixture.

The control or regulation of the flow rate of the gas mixture makes possible a flexible variation of the measuring method, as a result of which it is possible, for example, to achieve shorter measuring times, lower measuring inaccuracies, predetermined measuring times, expanded concentration ranges and/or an optimal and flexible utilization of the reaction chamber available.

According to a method variant, a temperature of the gas mixture flowing through the reaction chamber can be detected as a reaction rate parameter and the flow rate can be controlled or regulated as a function of the temperature of the gas mixture.

The adaptation of the measuring method to the temperature of the gas mixture makes an optimal measurement possible at different temperatures.

According to a method variant, a speed of a reaction front propagating in the direction of flow in the reaction chamber can be detected as a reaction rate parameter and the flow rate can be controlled or regulated as a function of the speed of the reaction front.

By adapting the flow rate, for example, of the mass flow or volume flow, an optimal speed of the reaction front can be obtained, as a result of which the measuring time, on the one hand, and the accuracy of the measurement, on the other hand, can be affected.

The speed of the reaction front propagating in the direction of flow in the reaction chamber is preferably regulated.

The course of the reaction can be optimally controlled in this way. For example, the regulation may be designed such that the entire reaction chamber is used for the propagation of the reaction front during a measurement in a predetermined time, as a result of which optimal measuring accuracy is made possible with a fixed measuring time.

According to a method variant, the gas mixture is delivered at a maximum flow rate at the start of the delivery of the gas mixture through the flow channel.

The measuring time is reduced by delivery at maximum flow rate, and a reaction front is formed in the reaction chamber if the component to be measured is present in the gas mixture. To achieve a desired measuring accuracy, the flow rate can be reduced in the further course of the measurement, as a result of which the speed of the reaction front is reduced and a sufficient number of measurement points can be recorded for the concentration determination.

The measuring method may comprise, furthermore, method steps according to which an intensity gradient of a reaction front propagating in the direction of flow in the reaction chamber is detected and the concentration of the component of the gas mixture is determined exclusively from optically detectable parameters, especially the reaction front and/or a temperature.

No additional sensors are necessary in this way besides the optical sensor for detecting additional measured values for the determination of the concentration, and a simple mode of construction of the measuring device is made possible.

Another variant of the measuring method comprises the method steps of detecting a speed of a reaction front propagating in the direction of flow in the reaction chamber during the delivery of the gas mixture; of determining and outputting a preliminary measurement result of the concentration of the component of the gas mixture from the speed of the reaction front during the delivery of the gas mixture; and of determining and outputting a final measurement result of the concentration of the component of the gas mixture after the end of the delivery of the gas mixture.

If the component to be measured is present in the gas mixture, a preliminary concentration is determined already at an early stage due to the detection of the speed of the reaction front. The user is thus informed in time that the chemical compound to be measured is present in the gas mixture, even if a desired accuracy of the measurement cannot yet be reached for determining a final measurement result. This is especially advantageous in case of chemicals that are hazardous for health, because, for example, corresponding protective measures can thus be taken more rapidly.

The measuring method preferably comprises the method steps of detecting a reaction front during the delivery of the gas mixture and of outputting a preliminary measurement result during the delivery of the gas mixture to indicate that at least a minimal concentration of the component of the gas mixture is present.

A preliminary measurement result can be outputted in this way already at the time of the first detection of the optically detectable reaction.

For example, the light with which the reaction chamber is illuminated may have a broad-band spectrum, and a plurality of color channels may be detected by the detection unit, and a weighting of the color channels may be performed during the analysis to determine the reaction front propagating in the direction of flow in the reaction chamber.

This makes it possible, on the one hand, to use a plurality of different optically detectable reactions between reactants and a plurality of chemicals, which reactions take place in the broad spectral range, for example, white light and/or infrared spectral range, and, on the other hand, to perform an optimized analysis of the respective optically detectable reaction selected in the selected reaction chamber by a correspondingly selected weighting of the color channels.

According to one method variant, the measuring method comprises the method steps of repeatedly performing the detection of the speed of the reaction front propagating in the direction of flow in the reaction chamber during the delivery of the gas mixture and of determining the preliminary measurement result of the concentration; of determining a quality index, especially a measuring inaccuracy, of the preliminary measurement results determined for the concentration; and of ending the delivery of the gas mixture if a minimum number of repetitions of the determination of the preliminary concentration measurement result was performed and the quality index is above a quality index threshold value, or the measuring inaccuracy is below a measuring inaccuracy threshold value.

A fast, dynamic measuring method is made possible in this way. The terms measuring inaccuracy and quality index will hereinafter be used essentially synonymously. The determination of the quality index may also be limited to certain selected ranges of the concentration measurement, for example, to an image quality, noise or variance in the estimated speed. It is also possible that the measuring inaccuracy threshold value can be selected by the user, as a result of which the user can select between faster measurements with a higher measuring inaccuracy or slower measurements with lower measuring inaccuracy.

According to another method variant, the measuring method comprises the method steps of detecting a reference image of the reaction chamber before the start of delivery of the gas mixture; of detecting a flow image of the reaction chamber after the start of delivery of the gas mixture; and of comparing the reference image and the flow image of the reaction chamber to determine the speed and/or an intensity gradient of a reaction front in the reaction chamber.

By comparing the flow image and the reference image, for example, by subtraction or standardization, it is possible, for example, to compensate a specific quality or positioning of the reaction chamber in the measuring device or to make possible a simple determination of the reaction front by means of standardized intensity threshold values.

It may also be possible that a reaction chamber is used for a second measurement and the speed of the reaction front is detected in a second partial area of the reaction chamber after a first measurement, in which a reaction front propagated exclusively in a first partial area.

A plurality of measurements can be performed in this way by means of a single reaction chamber. In particular, the measuring time and the flow rate or the speed of the reaction front can be controlled or regulated such that a plurality of measurements are possible with one reaction chamber. For example, the speed of the reaction front can be regulated such that a defined partial area of the reaction chamber, for example, one third of the reaction chamber, is passed through by the reaction front within a certain measuring time.

Another aspect of the present invention pertains to a measuring system with a measuring device described in the present application and with a reaction carrier, especially suitable for carrying out for a measuring method described in the present application.

The above-described embodiments may be combined with one another and with the above-described aspects as desired in order to achieve advantages according to the present invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
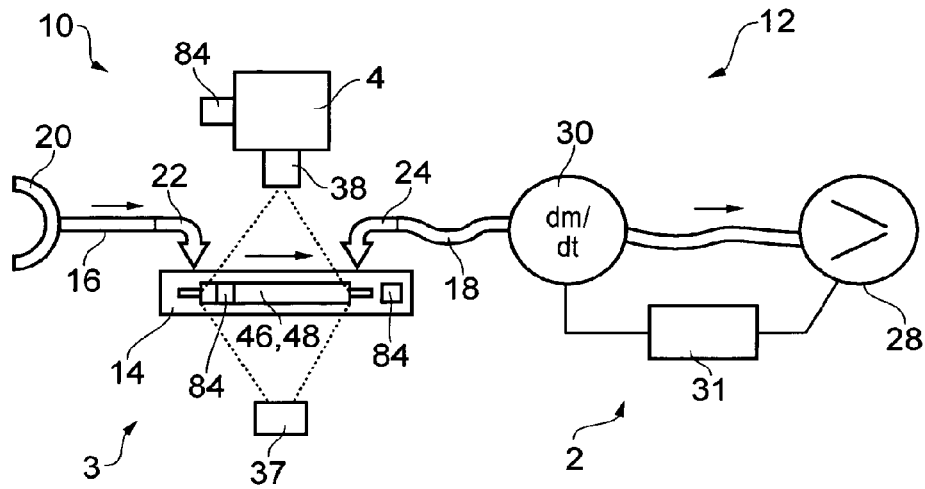
FIG. 1 is a schematic view of a first embodiment of a measuring system according to the present invention with a measuring device according to the present invention and with a reaction carrier according to the present invention.

FIG. 1 shows a schematic view of a gas-measuring system, hereinafter also called measuring system 10. The measuring system 10 comprises a measuring device 12 and a reaction carrier 14. The reaction carrier 14 has at least one flow channel, which forms a reaction chamber 46 with a reactant 48. The reactant 48 is designed to react with at least one component to be measured in a gas mixture or with a reaction product of the component to be measured in an optically detectable manner. The component to be measured can either react in this way directly with the reactant, or an intermediate reaction may be provided, in which the component to be measured reacts with an intermediate reactant and the reaction product formed in the process will subsequently react with the reactant in an optically detectable manner.

The measuring device 12 comprises a gas delivery unit 2 with a gas delivery device 28 for delivering the gas mixture through the flow channel 42 of the reaction carrier 14.

Furthermore, the gas delivery unit 2 comprises a gas inlet channel 16 with a gas port 24, which may be connected to the flow channel 42 of the reaction carrier 14. The gas delivery device 28 is arranged in the gas outlet channel 18 and makes possible the delivery of the gas mixture in a direction of flow indicated by arrows in FIG. 1.

A flow sensor 30 is arranged upstream of the gas delivery device 28 in the gas outlet channel 18 and detects, for example, a volume flow or a mass flow of the gas mixture flowing through the gas outlet channel 18.

A control/regulation unit 31 is provided, which is designed to control or regulate a flow of the gas mixture through the flow channel as a function of at least one reaction rate parameter. Reaction rate parameters may be, for example, the speed of propagation of a reaction front of the optically detectable reaction or a temperature of the gas mixture flowing through the flow channel 42. Temperature-measuring elements 84, which perform a measurement of the temperature of the gas mixture directly in the flow channel 42 of the reaction carrier 14 or indirectly by measuring the temperature of the reaction carrier 14 and/or of the measuring device 12, are provided for measuring the temperature of the gas mixture flowing through the flow channel 42.

The measuring device 12 comprises, furthermore, a detection unit 3 with a lighting device 37 for illuminating the reaction chamber 46 of the reaction carrier 14. The lighting device 37 is designed in the embodiment being shown to illuminate the reaction chamber with a broad-band spectrum. For example, the broad-band spectrum corresponds to white light. However, adjacent spectral ranges, as well as infrared spectral ranges or ultraviolet spectral ranges may also be comprised by the broad-band spectrum.

The detection unit 3 comprises, furthermore, an optical sensor 38 for detecting the optically detectable reaction in the reaction chamber 46 of the reaction carrier 14 as well as an analysis unit 4 for analyzing the data of the optically detectable reaction, which data are detected by the optical sensor, and for determining concentration of the component of the gas mixture.

The optical sensor 37 is a multichannel sensor, which can detect a plurality of color channels. The optical sensor 37 is designed in the embodiment being shown as a digital camera, and it will hereinafter also be called digital camera 38.

The analysis unit 4 is designed to perform a weighting of the color channels during the analysis of the data of the optical sensor 37.

Figure 2:
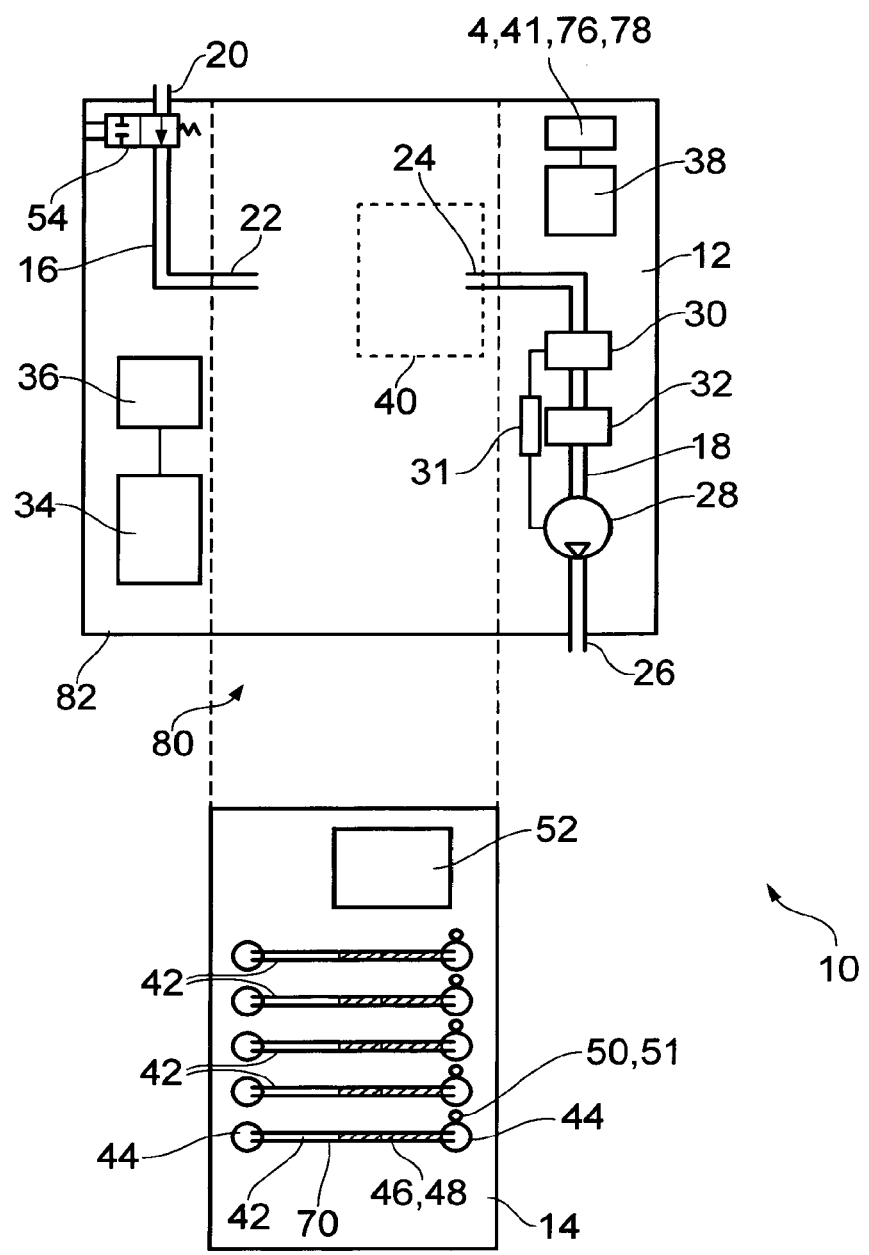
FIG. 2 is a detailed view of the measuring system from FIG. 1.

FIG. 2 shows a more detailed view of the measuring system 10 for measuring or detecting the concentration of gaseous and/or aerosol components. A replaceable reaction carrier 14, also called reaction carrier unit, is inserted manually by a user into the measuring device 12, also called gas-measuring device or otherwise gas-measuring system. The measuring system 10 and the measuring device 12 are a small, portable device, which can be used under mobile conditions and are provided with a battery as an energy supply.

The gas delivery device 28, which is embodied by a pump designed as a suction pump, is arranged on a housing of the measuring device 12. The housing forms, in addition, a mount, especially a sliding mount, for the displaceable reaction carrier 14. The reaction carrier can be moved within the housing of the measuring device by means of a reaction carrier delivery device 34 with a motor, e.g., an electric motor designed as a servomotor and a gear mechanism, especially driving roller, which is rotatable by the servomotor, because there is a mechanical contact or connection between the driving roller and the reaction carrier.

The measuring system 10 comprises the measuring device 12 and at least one reaction carrier 14. The gas inlet channel 16 extends from the gas mixture inflow opening 20 to the first gas port 22. The gas outlet channel 18 extends from the second gas port 24 to a gas mixture outflow opening 26.

The gas inlet channel 16 is made of glass, as a result of which a chemical reaction or a deposit of gaseous components on the wall of the gas inlet channel is prevented or reduced.

A valve 54 is arranged on the gas mixture inflow opening 20 upstream of the gas inlet channel 16. The valve makes possible, in its first position shown, a gas flow through the gas inlet channel 16 and prevents a gas flow through the gas inlet channel 16 in a second position. The valve 54 is designed as a 2/2-way valve in the embodiment shown.

The flow sensor 30, which is designed as a mass flow sensor in the embodiment being shown, makes possible the measurement of a gas flowing through the gas outlet channel 18. Both devices that measure the flow or the mass flow directly and those that detect other measured values and determine the flow or mass flow by means of these measured values may be used as flow or mass flow sensors.

Furthermore, a buffer 32, which makes possible a uniform gas flow through the gas outlet channel 18, is arranged in the gas outlet channel 18.

The measuring device 12 comprises, furthermore, a reaction carrier delivery device 34, which makes possible the movement of the reaction carrier 14 relative to the gas inlet channel 16 and the gas outlet channel 18.

A position sensor 36 is used to detect a relative position of the reaction carrier 14 and of the gas ports 22, 24.

The optical sensor 38 for detecting an optically detectable reaction is provided in the form of a digital camera 38 and makes possible the recording of the recording field 40 indicated by the dotted rectangle in FIG. 1.

A central control unit 41 is provided, which can process the data detected by the optical sensor and controls the measuring method. The central control unit comprises the analysis unit 4 in the embodiment being shown.

The reaction carrier 14 has a plurality of flow channels 42, which extend each between two connection elements 44. In the embodiment being shown, each of the flow channels 42 forms a reaction chamber 46, which is filled with reactant 48. The reactant 48 is a chemical compound, which reacts with a gas to be measured and/or with an aerosol component of a gas mixture in an optically detectable manner. This is, for example, a colorimetric reaction.

In the embodiment being shown, the flow channels 42 are filled each on their right side with the reactant 48. Another gas treatment element, for example, a desiccant, is provided on the left side of the flow channels 42.

A display pin 50, which forms a code 51, which is detected by the position sensor 36 and makes possible an independent positioning of the reaction carrier 14 in relative positions associated with the respective flow channels 42, is associated with each flow channel 42. Another type of code 51, for example, an electric, electronic or magnetic code, which can be detected by a corresponding position sensor 36, may also be provided. However, an optical code 51 is preferably provided at least additionally in order for a user of the measuring system 10 to be able to determine by looking at the reaction carrier 14 at a first glance whether the reaction carrier still has unused reaction chambers.

The reaction carrier 14 has, furthermore, an information field 52, on which information is stored. The information field 52 is designed in the embodiment being shown as an optical information field, in which information that can be read by the digital camera 38 is stored. As an alternative, the information field 52 may be provided as an electronic memory for information and designed, for example, as an RFID chip or SROM chip, which may be read and/or written on via electric contacts.

The recording field of the digital camera 38 is designed in the embodiment being shown such that the reaction chambers 46, the display pins 50 and the information field 52 are detected in the measuring device 12 by the digital camera 38 in at least one respective relative position of the reaction carrier 14. The digital camera 38 may be used in this way, on the one hand, for detecting the optically detectable reaction of the reactant 48 in the reaction chambers 46 of the reaction carrier 14 and, on the other hand, for reading the information in the information field 52 and as a position sensor 36 for detecting the relative position of the reaction carrier and the gas ports 22, 24. However, it is also possible that the position sensor 36 and a reading device for reading the information field 52 are designed as one device or as two separate devices.

Figure 3:
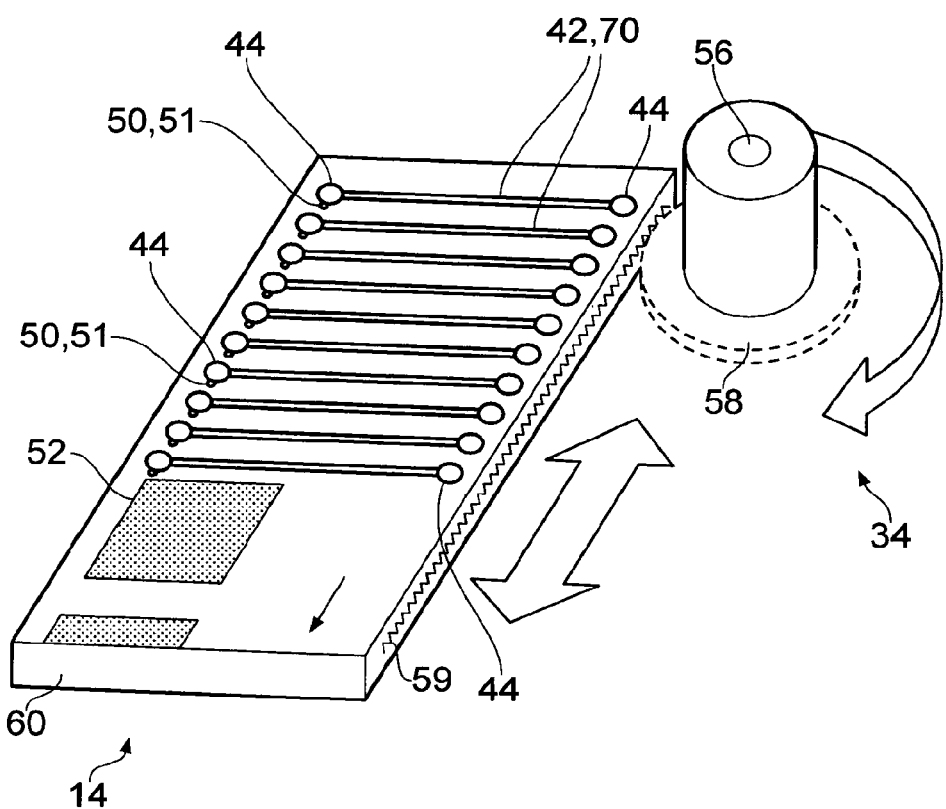
FIG. 3 is a detail view of a reaction carrier and a reaction carrier delivery unit.

FIG. 3 shows a schematic detail view of the reaction carrier 14 and of the reaction carrier delivery device 34 of the measuring device 12. The reaction carrier delivery device 34 comprises a servomotor 56 and a gear mechanism 58. The gear mechanism 58 comprises, for example, a gear wheel, which meshes with corresponding teeth 59 on the reaction carrier 14. The teeth 59 are formed on a housing 60 of the reaction carrier 14.

The reaction carrier delivery device 34 makes possible a relative motion of the reaction carrier 14 in two opposite directions, as a result of which any desired positioning of the reaction carrier 14 in the measuring device 12 is made possible. The reaction carrier 14 is preferably moved into and removed from the measuring device 12 through a single feed opening in a housing of the measuring device 12.

The reaction carrier 14 comprises a housing 60, which is transparent to light. Ten tubes designed as glass tubes are arranged on a top side of the housing 60, which top side is shown in FIG. 3, so that the tubes define a flow channel 42, and an identical reactant is arranged within this flow channel 42 or the tubes in the ten test tubes. At an end of the glass tubes shown on the right side in FIG. 3, these tubes have an inflow opening, and they have an outflow opening at an end of the glass tubes that is the left-hand end in FIG. 3. The inlet and outflow openings are sealed in a fluid-tight manner by a seal 64, for example, a glass seal. It is ensured hereby that the reactant within the glass tubes will not undergo any change in color on the reactant or the reactants because of an unintended and uncontrollable admission of gaseous and/or aerosol components to the reactant before the gas mixture is passed through the tubes by means of the gas delivery device 28, for example, a suction pump. The reactant is used, for example, to detect acetone, so that a change occurs in the color of the reactant when passing through a gas mixture containing acetone. A display pin 50 each is arranged in the area of the outflow openings. A display pin 50 is thus associated with each of the ten glass tubes. Furthermore, an optical code is also present as a matrix code or matrix bar code on the top side of the housing 60.

The inlet and outlet openings form, together with their seal 64, the connection elements 44 of the flow channels 52.

The gas ports 22 and 24 of the gas inlet channel 16 and of the gas outlet channel 18 as well as the corresponding connection elements 44 of the reaction carrier 14 will be described below on the basis of FIGS. 4 through 7.

Figure 4:
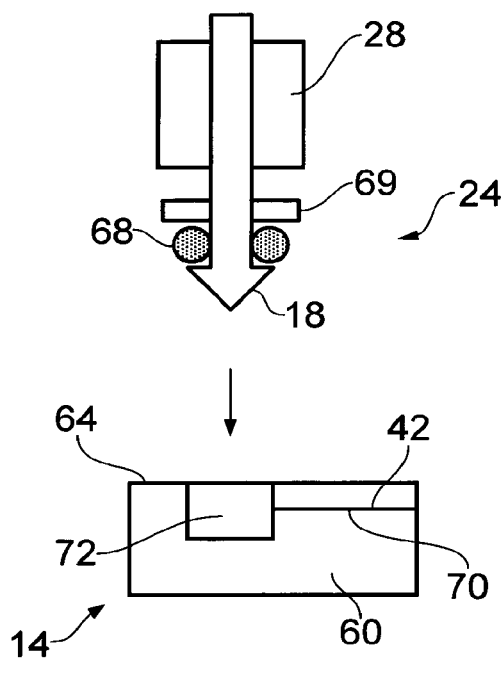
FIG. 4 is a detail view of a first embodiment of the gas port and of the connection element of the reaction carrier in a first position.
Figure 5:
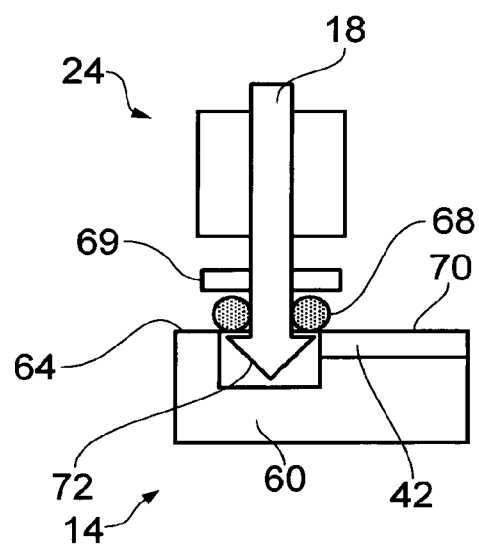
FIG. 5 is a detail view of a first embodiment of the gas port and of the connection element of the reaction carrier in a second position.

A first embodiment is described in FIGS. 4 and 5 as an example for the gas port 24 of the gas outlet channel 18. A gas connection piece of the gas outlet channel 18 and a seal 68 are arranged on the gas delivery device 28. An elastic sealing ring, for example, a rubber sealing ring, lies on the underside of a support ring 69 enclosing the gas connection piece and is fastened to the support ring 69, said sealing ring forming the seal 68. The support ring 69 has, in addition, an expansion as a display pin-moving element (not shown) at right angles to the drawing plane of FIGS. 4 and 5. FIG. 4 shows a first position of the gas port 24 and FIG. 5 shows a second position. No gas can be drawn in from the gas delivery device 28 through the glass tube of the flow channel 42 and the seal continues to be closed in the first position according to FIG. 4. During a motion of the gas port 24, the seal is first broken up or pierced by the gas connection piece and the sealing ring is then placed on the housing 60 and the glass tube on the outside, on the top side, so that the opening fitted into the seal is completely sealed. Moreover, the seal at the corresponding inflow opening of the glass tube is pierced by another connection piece of the other gas port 22 (not shown) and opened, so that the gas mixture can flow into the glass tube through the inflow opening. The gas delivery device 28 is subsequently activated and the gas mixture is drawn in as a result through the inflow opening, then sent around the reactant and the gas mixture is admitted to the reactant, and the gas mixture is subsequently delivered again into the surrounding area through the outflow opening, the gas connection piece and the gas delivery device 28.

Figure 6:
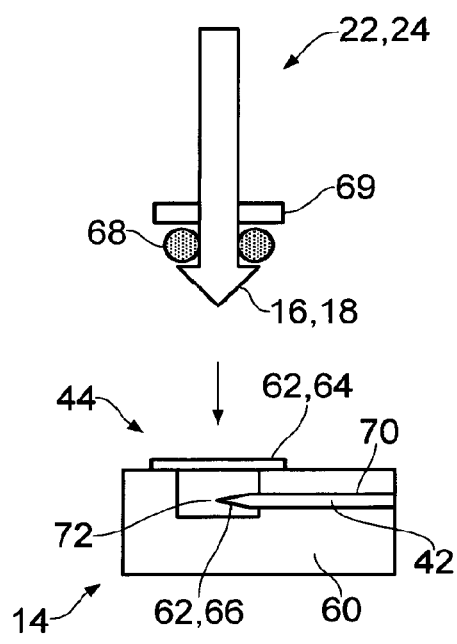
FIG. 6 is a detail view of a second embodiment of the gas port and of the connection element of the reaction carrier.
Figure 7:
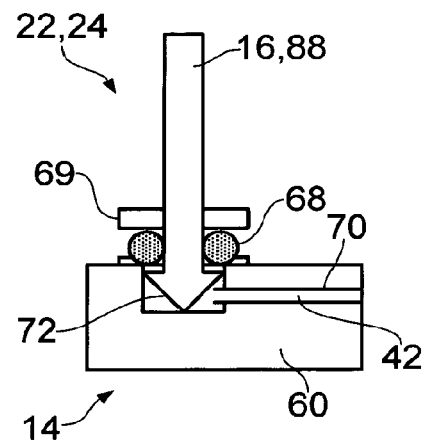
FIG. 7 is a detail view of a second embodiment of the gas port and of the connection element of the reaction carrier in a second position.

An alternative embodiment of the gas ports 22, 24 and connection elements 44 is shown in FIGS. 6 and 7. The connection elements 44 of the reaction carrier 14 comprise a sealing device 62 with a first seal 64 and with a second seal 66, which prevent gas from entering the flow channel 42. The flow channel 42 is formed by a tube 70, by a glass tube in the embodiment being shown, which is embedded in the housing 60 of the reaction carrier 14. The glass tube ends in a recess 72 in the housing 60. The recess 72 in the housing 60 is closed by the first seal 64. The first seal 64 is formed, for example, by a small glass plate or a film. The second seal 66 is formed by a closed end of the glass tube. The closed end of the glass tube of the flow channel 42 protrudes into the recess 72 in the housing 60.

The gas ports 22, 24 are formed at the end of the gas inlet channel 16 and at the beginning of the gas outlet channel 18. The gas port 22, 24 comprises a seal 68 and a gas connection piece. FIG. 6 shows the gas port 22, 24 in a starting position, in which the gas port 22,24 is separated from the connection element 44 of the reaction carrier 14. The gas port 22, 24 may be lowered in the direction of the reaction carrier 14 or, as an alternative, the reaction carrier 14 may be moved in the direction of the gas port. When lowering the gas port 22, 24, the lower end of the gas connection piece strikes the first seal 64 and pierces same. The seal 68 of the gas port 22, 24 subsequently comes into contact with the housing 60 of the reaction carrier 14 and forms a gas-tight seal of the recesses 72 of the connection element 44.

When the gas port 22, 24 is lowered further, the gas connection piece breaks off the closed end of the glass tube 70 of the flow channel 42 and opens in this way the second seal 66 of the connection element 44. FIG. 7 shows the end position of the gas port 22, 24, in which the connection between the gas port 22, 24 and the connection element 44 of the flow channel 42 is established.

It is possible, as an alternative, that the first seal 64 has, for example, a flexible design, so that the first seal 64 is pierced only when the seal 68 of the gas port 22, 24 is already sealingly in contact with the housing 60 of the reaction carrier 14. It is also possible that the seal 68 is designed such that it first comes into contact with the housing 60 of the reaction carrier 14 to seal the recess 72. Further, it is also possible that only one of the seals 64 or 66 of the sealing device 62 is provided on the connection element 44 of the reaction carrier 14.

Figure 8:
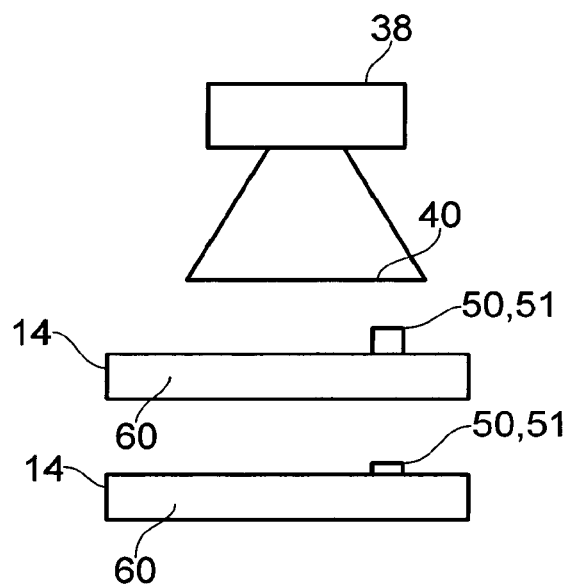
FIG. 8 is a side view of the digital camera, of the reaction carrier with a display pin in a first position and of the reaction carrier with the display pin in a second position.
Figure 9:
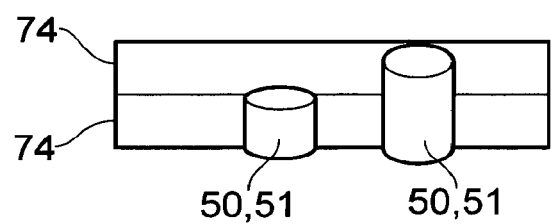
FIG. 9 is a perspective view of the display pin in a first position and of the display pin in a second position.

The code 51 of the reaction carrier 14 for the independent positioning of the reaction carrier 14 in a plurality of different relative positions in the measuring device 12 will be described below on the basis of FIGS. 8 and 9.

The position sensor 36 for detecting the relative position of the reaction carrier 14 and the gas ports 22, 24 is embodied in the embodiment being shown together with the optical sensor for detecting the optically detectable reaction of the reactant 48 by the digital camera 38. No separate component is thus needed for the function of the position sensor. However, it is also possible that a non-optical position sensor, for example, an electric or magnetic position sensor, which can detect a corresponding code 51 of the reaction carrier 14, is provided.

The detection of the position of the reaction carrier 14 is likewise performed in a simple manner by means of the digital camera 38, because the analysis unit has a corresponding optical software, by means of which the position of the reaction carrier 14 can be determined on the basis of the data detected by the digital camera. The gas port 22, 24 is subsequently moved downwards, so that the seal is pierced thereby by the gas connection piece and the gas mixture can be drawn in through the outflow opening. The display pin 50 is additionally moved now by an expansion or display pin-moving element of the support ring (not shown) of the support ring from a first position according to the upper reaction carrier 14 in FIG. 8 into a second position according to the lower reaction carrier 14 in FIG. 8. In the first position of the display pin 50, said pin projects farther out of the housing 60 of the reaction carrier than in the second position. The position of the display pin 50 may also be detected with the digital camera, and the display pin has another color, for example, orange, different from the rest of the reaction carrier 14; for example, the housing 60 is colored at least partially blue. The digital camera 38 has two separate ROIs (regions of interest), i.e., partial areas 74 of the recording field 40 of the digital camera 38, so that the color orange appears in the partial area 74 that is the upper area in FIG. 9 in the first position and no color or a substantially smaller quantity of the color of the display pin 50 appears on the upper partial area 74 in the second position. As a result, it can be detected by the optical analysis software of the analysis unit of the central control unit 41 whether a display pin 50 is in the first or second position. Based on this detection of the first or second position of the display pin 50, the reaction carrier delivery unit 34 is moved, furthermore, independently and automatically by the servomotor 56 into such a position that the first, hitherto unused glass tube, through which no gas mixture has hitherto been passed, is located with the outflow opening above the gas connection piece of the gas port 22, 24, and it is only thereafter that the gas port 22, 24, especially the suction pump and the gas connection piece, are moved downwards corresponding to FIGS. 4 and 5.

The display pin 50 is always arranged adjacent to the connection elements 44 at the edge of the reaction carrier 14 in the embodiment being shown. The display pin 50 is thus located in the edge area of the recording field 40 of the digital camera 38 and is thus detected by the digital camera 38 obliquely at an angle, as a result of which the height of the display pin can be detected.

On the one hand, the digital camera 38 and the optical analysis software can detect in this way a position of a display pin 50 and thus approach any desired relative position of the reaction carrier 14 in the measuring device 12 via the reaction carrier delivery device 34. On the other hand, the information on whether the corresponding flow channel 42 has already been used or not can be read based on the height of the display pin 50.

Instead of an optical code 51, it is also possible to provide, for example, an electric or magnetic code 51, which may be embodied, for example, by means of an electrically conductive field on the surface of the housing 60.

Figure 10:
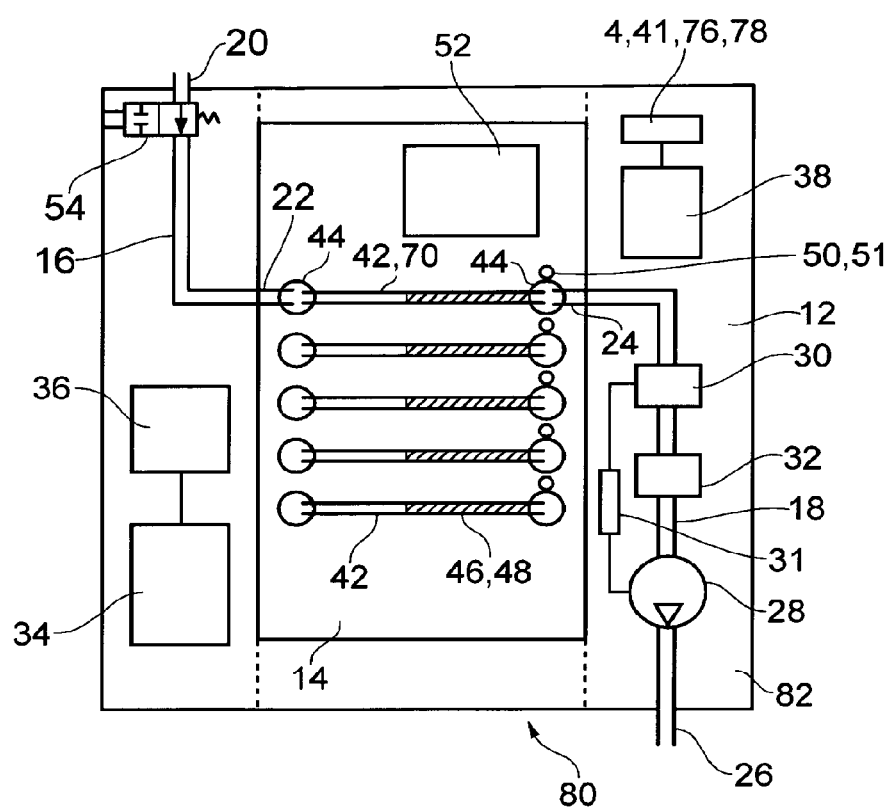
FIG. 10 is a schematic view of the measuring system according to FIG. 2, in which the reaction carrier is in a position in the measuring device.

The measuring system 10 according to FIG. 2, is shown in FIG. 10 with the reaction carrier 14 positioned in the measuring device 12. The gas delivery unit 2 is connected via the gas ports 22, 24 to a flow channel 42 of the plurality of identically designed flow channels 42 of the reaction carrier 14, for delivering the gas mixture through the flow channel 42. According to FIG. 10, the flow channel 42 is the first flow channel in the insertion direction.

Figure 11:
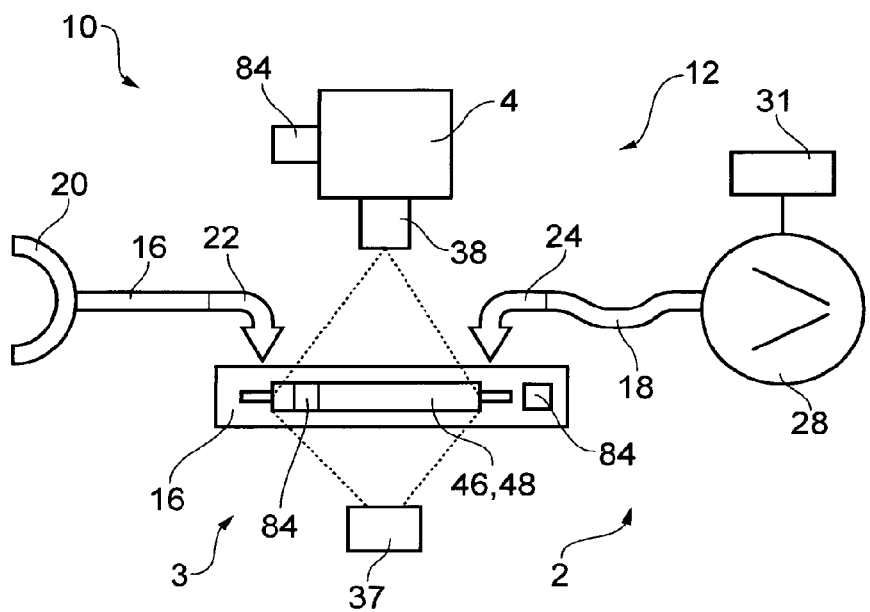
FIG. 11 is a schematic view of a second embodiment of a measuring system according to the present invention.

FIG. 11 shows an alternative embodiment of the measuring device 12, which differs from the embodiment shown in FIG. 1 essentially in that no flow sensor 30 is provided in the gas outlet channel 18. The detection unit 3 is designed, by contrast, to detect an intensity gradient of the reaction front 6 propagating in the direction of flow in the reaction chamber 46. The detection unit 3 comprises, furthermore, an analysis unit 4, which is designed to determine the concentration of the component to be measured in the gas mixture exclusively from the optically determinable parameters of the reaction front.

A measuring method will be described below with reference to the embodiment according to FIGS. 2 and 10.

The reaction carrier 14 is inserted into an insertion opening 80 in a housing 82 of the measuring device 12. The reaction carrier 14 is inserted manually into the insertion opening, detected by the reaction carrier delivery device 34 and transported forward in the insertion direction.

The information field 52 of the reaction carrier 14 passes through the recording field 40 of the digital camera 38 during the transportation of the reaction carrier 14, and the information contained on the information field 52 is detected by the digital camera 38 and can be analyzed in an analysis unit of the central control unity 41. It is also possible that the reaction carrier is positioned in a reading position, in which reading of the information field 52 is made possible. The information on the information field 52 is stored optically in the embodiment being shown and can thus be read by the digital camera 38 in a simple manner. It is also possible, as an alternative, that an electronic information field 52 is provided, which is designed, for example, as an active or passive RFID chip or SRAM chip and can be read in a wireless manner or via electric contacts. The electric contacts are preferably established via data lines to the inflow and outflow openings of the flow channels 42 and gas connection pieces consisting of a current-carrying material, so that a current and data connection is established between the SRAM chip and a corresponding reading device, while the gas connection pieces are located in the inflow and outflow openings.

The information of the reaction carrier 14, which is contained on the information field 52, especially relating to the component to be measured in the gas mixture and a corresponding concentration range, is read in a first method step.

The reaction carrier 14 is subsequently positioned in a relative position relative to the gas ports 22, 24 of the measuring device 12, and a flow channel 42 that has an unused reaction chamber 46 is selected, the flow channel selected being the flow channel 42 of the reaction carrier 14 that is the first flow channel in the insertion direction in the example shown in FIG. 10.

A connection is established between the gas ports 22, 24 through the second flow channel 42, and the gas delivery device 28 delivers a gas mixture to be measured through the outlet channel 18, the second flow channel 42 and the gas inlet channel 16, and the digital camera 38 detects a possible optically detectable reaction in the reaction chamber 46.

The detection unit 3 detects a reaction front 6 propagating in the direction of flow in the reaction chamber 46 and the speed thereof during the delivery of the gas mixture and determines a preliminary measurement result of the concentration of the component to be measured in the gas mixture from the speed of the reaction front 6.

A final measurement result of the concentration of the component of the gas mixture is determined and outputted after the end of the delivery of the gas mixture.

If the component to be determined in the gas mixture is not present in the gas mixture or is present at a concentration below a detection threshold of the concentration range of this reaction carrier 14, no optically detectable reaction is detected in the reaction chamber 46, i.e., no reaction front 6 develops in the reaction chamber 46.

A corresponding result of the measurement is displayed by the measuring device, for example, optically or acoustically.

A checking is preferably performed for leakage flows whenever a connection is established between the gas ports 22, 24 via a flow channel 42.

In a first step, the gas port 24 of the gas outlet channel 18 is connected to the corresponding connection element 44 of the reaction carrier 14. In a second step, gas is delivered through the gas outlet channel 18 and the flow channel 42 of the reaction carrier 14, which said flow channel is connected thereto, and the gas flow through the gas outlet channel is measured to check for leakage flows. If the system comprising the gas outlet channel and the flow channel is gas-tight, no gas flow is measured essentially through the gas outlet channel 18, because the flow channel 42 of the reaction carrier 14 is closed in a gas-tight manner via the second connection element 44 closed by the sealing device 62.

The gas inlet channel 16 is closed upstream by the valve 54 in a further step and the gas port 22 of the gas inlet channel 16 is connected to the corresponding connection element 44 of the reaction carrier 14. Gas is subsequently delivered by the gas delivery device 28 through the gas outlet channel 18, the flow channel 42 and the gas inlet channel 16, and the gas flow through the gas outlet channel is measured for checking for leakage flows. If the system comprising the gas outlet channel 18, the flow channel 42 and the gas inlet channel 16 is gas-tight, no gas flow is measured essentially through the gas outlet channel 18, because the gas inlet channel 16 is closed by the valve 54 in a gas-tight manner.

The measurement of an essentially zero gas flow during the measurement described in the preceding paragraphs in a gas-tight measuring system 10, in which normal pressure is present in the gas outlet channel 18, the flow channel 42 and/or the gas inlet channel 16 before the checking for leakage flows, should be interpreted such that an essentially exponentially decreasing gas flow following the vacuum is measured. In other words, the measured gas flow in a gas-tight measuring system 10 corresponds to the quantity of gas that is present in the channels 16, 18, 42 at the start of the measurement and that is pumped off through the gas delivery device 28 at the time of the checking for leakage flows.

If a leakage flow, i.e., a gas flow exceeding the gas flow mentioned in the preceding paragraph, is measured through the gas outlet channel 18, a corresponding error message is sent by the measuring device 12. The flow channel 42 on the reaction carrier 14 or gas outlet channel 18 and gas inlet channel 16 of the measuring device 12 can then be checked, for example, by the user.

It is also possible that both gas ports 22, 24 of the gas outlet channel 18 and of the gas inlet channel 16 are connected to the corresponding connection elements 44 of the flow channel 42 already in a first step and a single checking for leakage flows is correspondingly performed.

Figure 12:
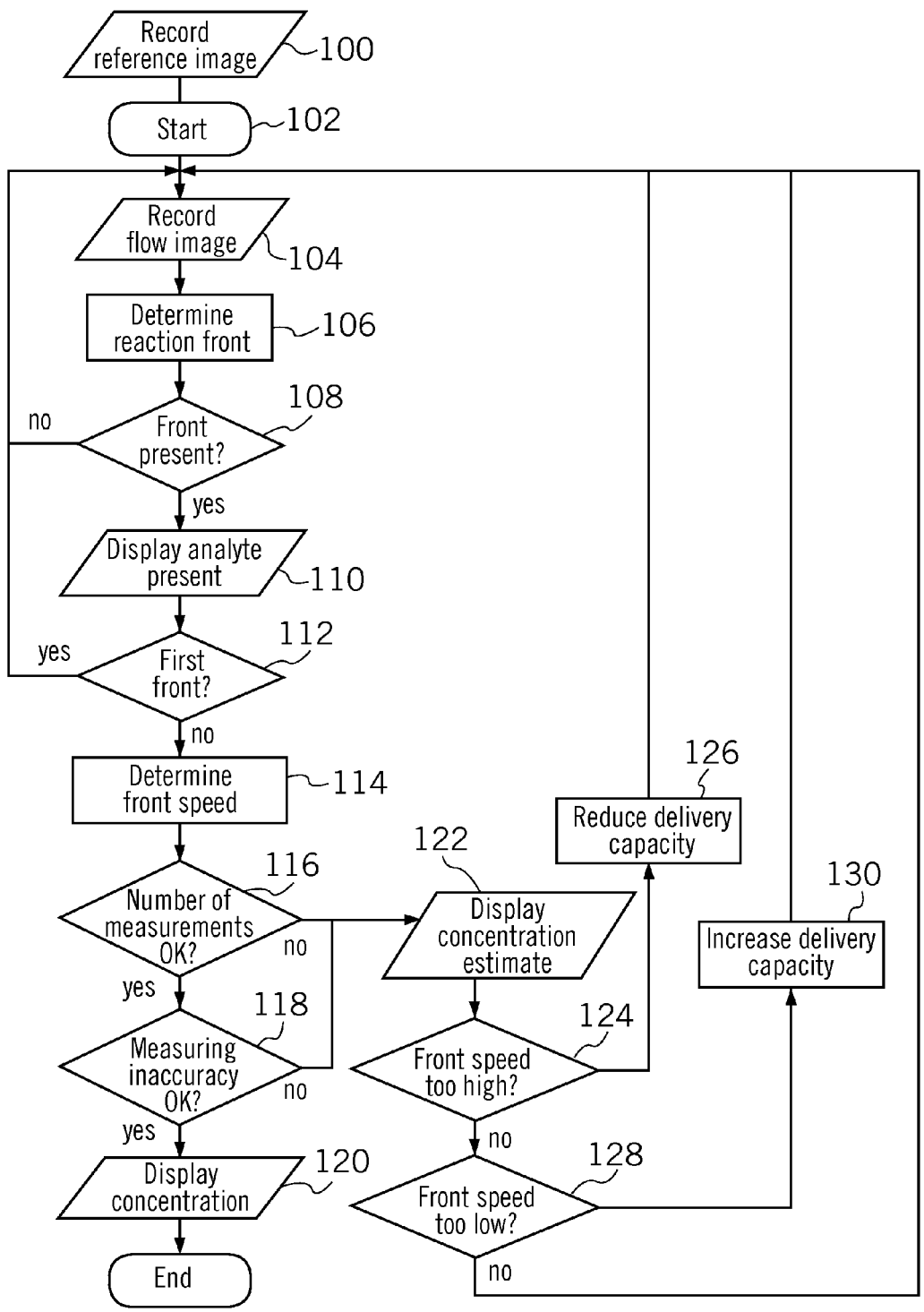
FIG. 12 is a flow chart of a measuring method according to the present invention.

The method steps of a measurement will be described below on the basis of the flow chart shown in FIG. 12.

After the reaction carrier 14 has been positioned with an unused reaction chamber 46 at the gas ports 22, 24 of the measuring device 12, the reaction chamber 46 is illuminated with a broad-band spectrum, white light in the exemplary embodiment.

A reference image of the reaction chamber 46 and of the reactant 48 contained therein is recorded in step 100 before the start of delivery of the gas mixture.

In the subsequent method step 102, the gas delivery device 28 starts to deliver the gas mixture through the flow channel 42 at a time T0.

The control/regulation unit 31 controls or regulates the flow rate of the gas mixture through the flow channel 42 as a function of a reaction rate parameter. Delivery is preferably performed at a maximum flow rate at the start of the method in the method variant being shown. The shortest measuring time possible is obtained in this way, because the component to be measured is not present in the gas mixture at all in many measurements. A necessary volume of the gas mixture to reach the detection threshold can be delivered rapidly through the reaction chamber due to the high flow rate. In measurements in which the component to be measured is present in the gas mixture and a reaction front will thus develop in the reaction chamber, the speed of propagation of this reaction front may be too high in case of the maximum flow rate. Provisions are made in such a case for effecting a corresponding reduction of the delivery capacity of the gas delivery device 28 in order to achieve a sufficient accuracy for the determination of the concentration of the component of the gas mixture, cf. method steps 116 and 118 in the following method.

A reaction rate parameter may be a temperature of the gas mixture flowing through the reaction chamber 46. The detection unit 3 is designed to determine the temperature of the gas mixture and to transmit this to the control/regulation unit of the gas delivery unit 2 in order to control or regulate the flow rate as a function of the temperature of the gas mixture. For example, the reaction between the component of the gas mixture and the reactant is expected to be fast at a high temperature of the gas mixture. A lower flow rate may correspondingly be provided at high temperatures already at the start of the delivery of the gas mixture. Furthermore, it is possible to measure or calculate the course over time of the temperature of the gas mixture flowing through the reaction chamber 46 and to provide for a corresponding time-dependent control or regulation of the flow rate.

The temperature of the gas mixture flowing through the reaction chamber 46 may be measured, for example, directly in the flow channel 42 of the reaction carrier 14, for example, via temperature sensors or thermochromic substances, which undergo a temperature-dependent, optically detectable change. It is possible, as an alternative, to measure the temperature of the reaction carrier 14 and/or of the measuring device 12. The transported quantity of heat of the gas mixture may be considered to be negligible compared to the quantity of heat of the reaction carrier or the measuring device and it may be assumed that the gas mixture in the reaction chamber has essentially the temperature of the reaction carrier 14.

It is possible that the measuring device 12 and the reaction carrier 14 have equal temperature at the start of the measuring method, in which case the temperatures of the measuring device 12 and reaction carrier 14 become equal after insertion of the reaction carrier 14 into the measuring device 12. A corresponding temperature course over time may be calculated by modeling the heat transfer, for example, by means of an exponential function.

In a further method step, the digital camera 38 records flow images of the reaction chamber 46 through which gas mixture flows at regular intervals, and method step 104 represents the recording of one flow image each. An exemplary flow image is shown in the upper section of FIG. 13. The x axis corresponds to the direction of flow of the gas mixture in the flow channel 42, which is indicated by the arrow above the flow image.

An analysis of the flow image and a determination of the parameters of the reaction front takes place in the flow chart in method step 106.

The image data of the flow image are analyzed by taking the mean in the y direction, i.e., the mean of all intensity values of one column is taken, so that a mean intensity value is available for each point on the x axis.

Moreover, the flow image is compared to the reference image recorded in step 100. A difference of the intensity values of the two images is formed for this in the method variant being shown. As an alternative, the flow image may also be standardized by the intensity values of the reference image. Interference effects, which arise, for example, from the positioning of the reaction chamber 46, the illumination of the reaction chamber 46 and/or the special arrangement of the reactant 48 in the reaction chamber 46, can be avoided in this way.

Figure 13:
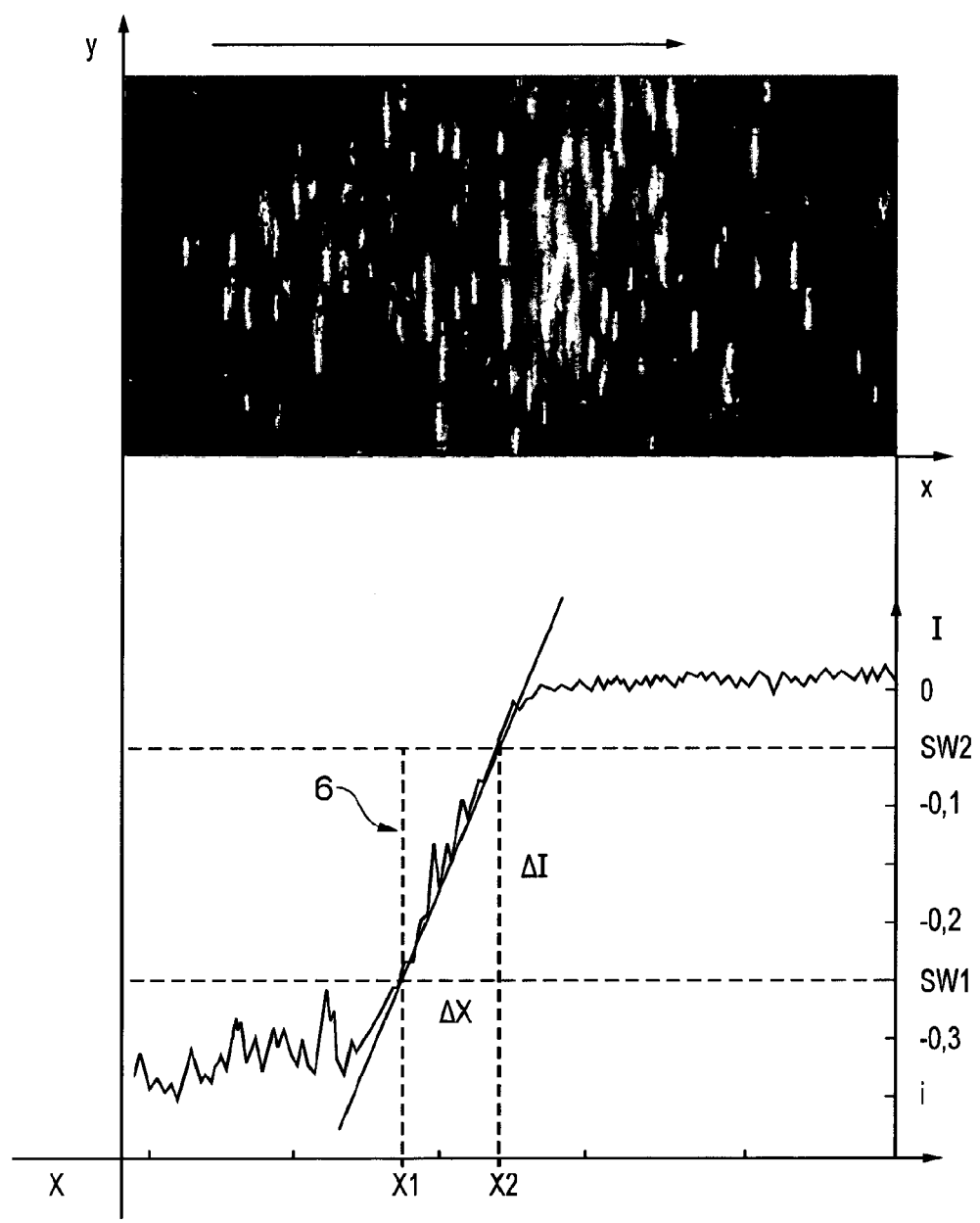
FIG. 13 is a flow image of the reaction chamber and a corresponding intensity curve.

The intensity curve shown in the lower section of FIG. 13 is obtained after these image processing steps.

The flow image shown in FIG. 13 shows the reaction chamber 46, in which a reaction front 6 of an optically detectable reaction taking place between the reactant 48 and the component to be measured in the gas mixture, which reaction front propagates in the direction of flow, has approximately reached the middle area of the reaction chamber 46.

The intensity value, i.e., the difference between the intensities of the flow image and the reference image in the embodiment being shown, is approximately zero in the right-hand area of the reaction chamber 46, in which no optically detectable reaction of the reactant 48 has taken place as yet.

The intensity value drops to a value below −0.3 in the middle area of the reaction chamber 46. This area forms the reaction front and hence the area of the reaction chamber 46 in which the optically detectable reaction between the reactant 48 and the component to be measured in the gas mixture takes place.

In the left-hand area of the reaction chamber 46 the intensity value is at a level of about −0.30 to −0.35. The reactant 48 has reacted approximately completely with the component to be measured in the gas mixture in this area, and depletion of the reactant 48 appears.

A position X1 of the reaction front 6 is determined in a simple manner via a threshold value SW1 in the method variant being shown. For example, position X1 of the reaction front 6 is placed now on the first position, at which the intensity value is below the threshold value SW1, which equals −0.25 in this case. It is possible, as an alternative, to adapt a suitable function to the intensity curve and to obtain a position of the reaction front in this way.

Moreover, an intensity gradient of the reaction front is determined from the intensity curve. The position X2, at which an upper threshold value SW2 of −0.05 is reached, is additionally determined for this in the exemplary embodiment being shown.

For example, the intensity gradient is determined from the flow ($\Delta I/\Delta X$) of the straight line passing through these points. It is possible, as an alternative, to calculate the intensity gradient by means of linear regression of the corresponding sections between X1 and X2.

Furthermore, a suitable function can be adapted to the entire intensity curve, especially the function used to determine the position of the reaction front, and the selected function makes it possible to determine an indicator of the intensity gradient of the reaction front.

A checking is performed in a subsequent method step 108 to determine whether a reaction front is present in the respective flow image. If there is no reaction front, the method goes back to step 104 and the next flow image is recorded.

If, by contrast, a reaction front is present, the method goes to step 110, in which it is displayed to the user of the measuring device 12 that at least a minimum concentration of the component (analyte) to be measured in the gas mixture is present in the gas mixture. The user is warned in this way very early in the course of the measurement that the analyte is present in the gas mixture and can take corresponding protective measures in case of hazardous substances. A reaction front 6 develops at the time T1 in the measured data shown in FIG. 15.

A checking is performed in method step 112 to determine whether the reaction front present in the flow image recorded at that time is the first reaction recorded until that point in time. If the current flow image is the first flow image, because a reaction front could be detected, the speed of the reaction front cannot be reliably determined, and the method proceeds further with the recording of the next flow image in step 104. However, it is also possible that a rough estimation of the speed of the reaction front is performed from the position of the reaction front and the time interval from the preceding flow image without reaction front.

Figure 14:
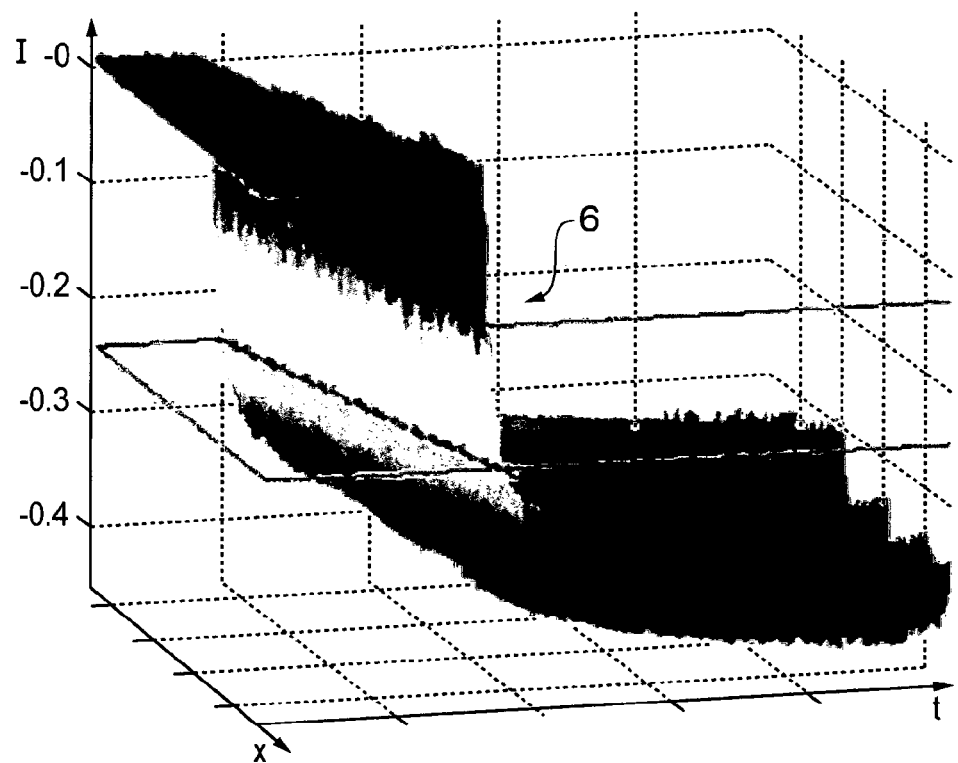
FIG. 14 is a three-dimensional view of a time series of the intensity curves.

If, however, a reaction front was already detected in the preceding flow image, the method proceeds to step 114, in which a speed of the reaction front is determined. The determination of the reaction front will be described below on the basis of FIGS. 14 and 15. FIG. 14 shows a three-dimensional view of the time series of the intensity curves of the flow images recorded one after another. The x direction of the reaction chamber 46 is in the direction of flow in FIG. 14 and the time t is plotted in a plane to which the axis of the intensity values I is directed at right angles.

The particular position of the reaction front is determined analogously to FIG. 13 based on the threshold value, the threshold value SW1 being shown in FIG. 14 by a plane at an intensity value of −0.25.

Figure 15:
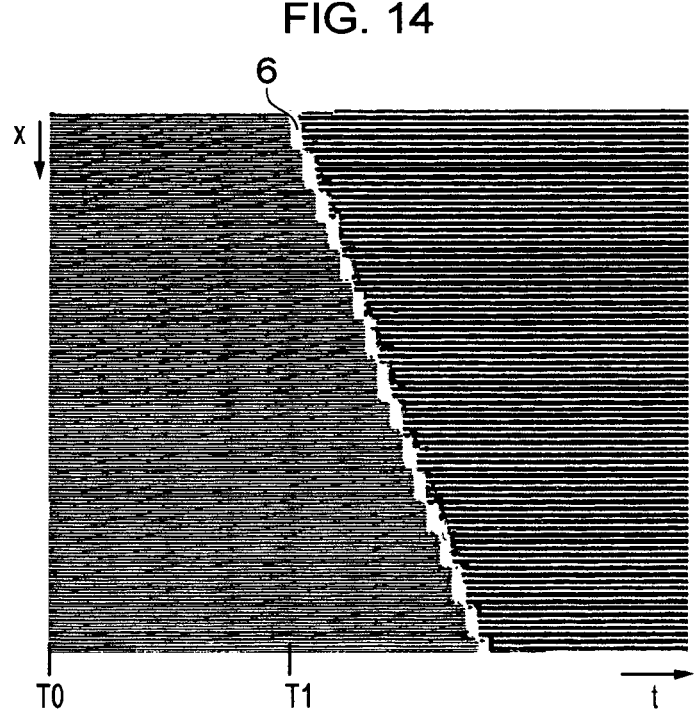
FIG. 15 is a two-dimensional view of the time series from FIG. 14.

FIG. 15 shows a corresponding two-dimensional view, in which the high intensity values are represented by the narrow hatching and the low intensity values by the broad hatching. The areas of the reaction front 6 are always shown without hatching. The positions of the reaction fronts, which are determined for each flow image, are located approximately on a straight line. A corresponding speed of the reaction front 6 can be determined by linear regression.

A preliminary concentration of the component to be measured in the gas mixture as well as its measuring inaccuracy are determined in the measuring device 12 shown in FIG. 1 from the determined speed of the reaction front and the flow rate measured by the flow sensor 30.

For the measuring device 12 shown in FIG. 11, the measuring method comprises, furthermore, the detection of the intensity gradient of the reaction front propagating in the direction of flow in the reaction chamber 46, which detection is described in FIG. 13, and the determination of the concentration of the component to be measured in the gas mixture exclusively from the optically detectable parameters of the reaction front. This is performed, for example, by means of the following partial differential equation:

$$\frac{\partial c_a}{\partial t} = -v_0 \frac{\partial c_a}{\partial x} + r_a$$

in which $c_a$ is the distribution of the concentration of the component (analyte) to be measured in the reaction chamber 46, $v_0$ is a flow velocity of the gas mixture through the reaction chamber and $r_a$ is a parameter dependent on the concentration of the component to be measured in the gas mixture.

The distribution of the concentration of the component to be measured in the reaction chamber 46 may be assumed to be essentially proportional to the intensity value in the area of the reaction front 6. The partial derivations of the concentration distribution according to time and according to the site can be determined from the speed of the front and from the intensity gradient in the area of the reaction front. By adapting the partial differential equations to the measured data, respective measured values can be determined for $v_0$ and $r_a$. The concentration of the component to be measured in the gas mixture can be determined from these measured values by means of calibrated characteristic diagrams. No separate flow sensor 30 is needed in this way, as a result of which the simple mode of construction of the measuring device 12 according to FIG. 11 is made possible.

A checking is performed in a subsequent method step 116 to determine whether the number of flow images recorded with detected reaction front is sufficient to reach a desired maximum measuring inaccuracy. If the number of flow images recorded up to this point with detected reaction front is too low, the method continues with method step 122.

If a sufficient number of flow images with detected reaction front has basically been recorded, the measuring method checks in step 118 whether the measuring inaccuracy of a preliminary concentration, which is determined from the speed of the reaction front, which speed was detected on the flow images recorded hitherto, is below a measuring inaccuracy threshold value.

If, by contrast, the measuring inaccuracy is below the measuring inaccuracy threshold value, the measuring method proceeds with step 120, in which the delivery of the gas mixture through the flow channel is ended and the determined concentration of the component of the gas mixture is displayed as a final measurement result together with the measuring inaccuracy or a quality index.

If the measuring inaccuracy of the preliminary concentration is above the measuring inaccuracy threshold value, the method continues with method step 122.

The preliminary concentration of the component to be measured from the speed of the reaction front is displayed to the user in method step 122. A preliminary concentration is displayed in this way early in the measuring method to the user. It is also possible to indicate a corresponding measuring inaccuracy to the user. By recalculating the concentration each time a new flow image is recorded, the user will thus receive real-time information on the course of the measuring method.

Figure 16:
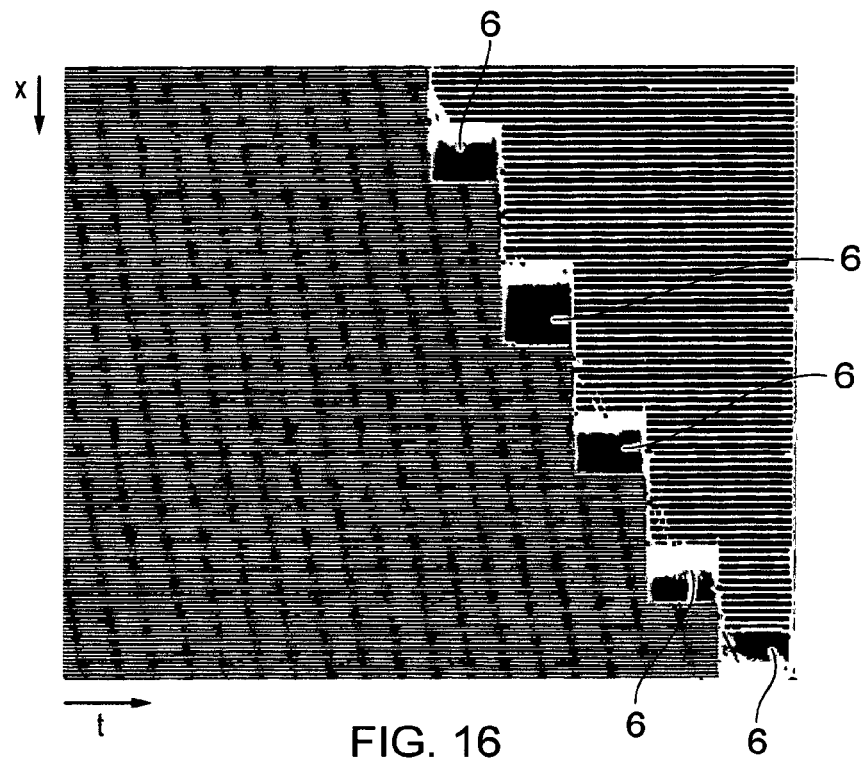
FIG. 16 is a two-dimensional view of a time series of intensity curves with high speed of a reaction front.

The flow rate of the gas mixture through the flow channel 42 is controlled or regulated in method steps 124, 126, 128 and 130 as a function of the speed of the reaction front. FIG. 16 shows a measurement at a high front speed, at which only a few flow images with a reaction front could be determined, because the reaction front has passed through the reaction chamber too fast. This leads to an increased measuring inaccuracy of the measurement of the concentration. On the other hand, an excessively low front speed may have an adverse effect on the measuring time.

It is checked in method step 124 whether the front speed is too high. If an excessively high front speed is found, the delivery capacity of the gas delivery device 28 is reduced in the subsequent method step 126. The flow rate in the flow channel 42 is reduced in this way and the front speed decreases, so that a greater number of measurement points can be correspondingly recorded.

It is checked in method step 128 whether the front speed is too low. In case of an excessively slow front speed, which would lead to a long measuring time, the delivery capacity of the gas delivery device 28 is increased in the next method step 130. The flow rate in the flow channel 42 is increased in this way, as a result of which the front will increase and the measuring time can be reduced.

A change in the flow rate is taken correspondingly into account when analyzing the measured data, especially when determining the speed of the reaction front.

Both the method steps 124 and 126 and the method steps 128 and 130 are provided according to the method variant shown in the flow chart. A regulation of the speed of the propagating reaction front is essentially performed in this way. However, it is also possible, as an alternative, that only a simple control or regulation of the flow rate of the gas mixture takes place as a function of the speed of the propagation reaction front. This is possible, for example, by providing only one of the two pairs of method steps 124, 126 or 128, 130 in the measuring method.

The speed of the propagating reaction front thus forms one of the reaction rate parameters, as a function of which the control/regulation unit 31 controls or regulates the flow rate of the gas mixture. A simple control of the delivery capacity of the gas delivery device 28 takes place in a simple method variant. As an alternative, the flow rate may be regulated via the flow sensor 30.

If the front speed is neither too high nor too low, the method continues in step 104 with the recording of the next flow image.

The measuring method is thus designed for the repeated performance of method step 114, which contains the detection of the speed of the reaction front propagating in the direction of flow in the reaction chamber during the delivery of the gas mixture and during the determination of the preliminary measurement result of the concentration. A measuring inaccuracy of the preliminary measurement results of the concentration is determined in the method steps 116 through 120, and the delivery of the gas mixture is ended if a minimum number of repetitions of the determination of the preliminary measurement result of the concentration was performed and the measuring inaccuracy is below a measuring inaccuracy threshold value.

A fast, dynamic measuring method is obtained in this way. It is possible that the measuring inaccuracy threshold value can be selected by the user, as a result of which the user is able to choose between faster measurements with higher measuring inaccuracy or slower measurements with lower measuring inaccuracy.

Figure 17:
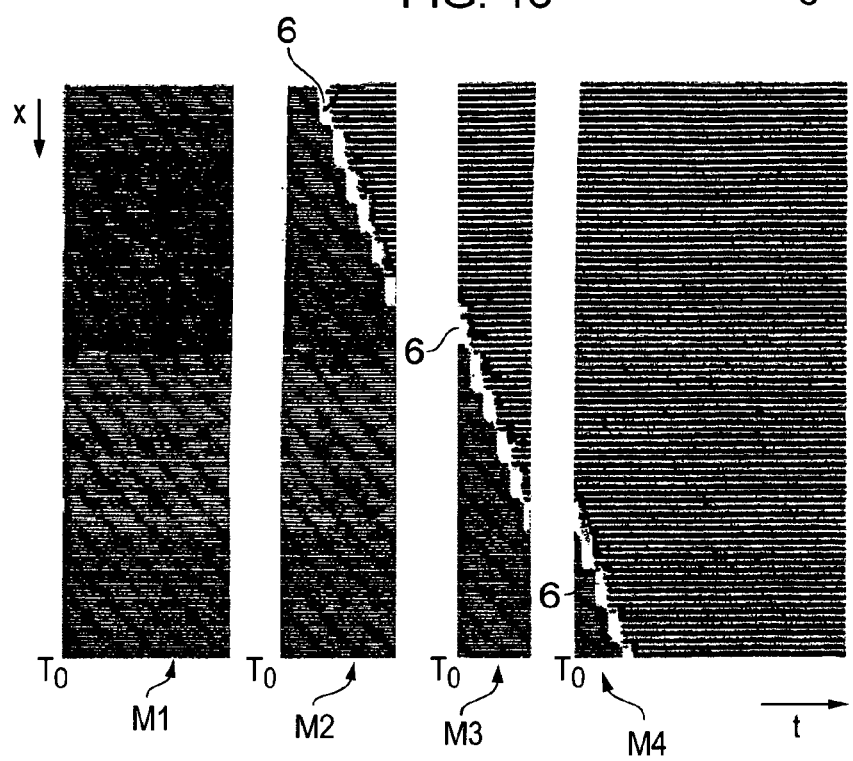
FIG. 17 is a two-dimensional view of a time series of intensity curves with a plurality of measurements with the use of one reaction chamber.

The measurement was continued in the reaction chambers shown in FIGS. 15 and 16 until the reaction front had passed over the entire length of the reaction chamber. It is, however, also possible according to the above-described method to carry out a plurality of consecutive, different measurements with a single reaction chamber, as this is shown in FIG. 17.

In a first measurement M1, the component to be measured was not present in the gas mixture and no reaction front developed. The component to be measured was present in the gas mixture in the second measurement M2 and a first reaction front developed. After the reaction front passed through a first partial area of the reaction chamber, a sufficient number of flow images could be recorded, and the measuring inaccuracy was below the measuring inaccuracy threshold value, so that the measurement was stopped and the final measurement result was outputted. A reference image, which corresponds essentially to the last flow image of the preceding measurement, is recorded for the third and fourth measurements M3 and M4 each.

In case a reaction front developed during the respective preceding measurement, the first flow images of the subsequent measurement can be ignored for the determination of a reaction rate in order to be on the safe side that the reaction front is not formed by residual gases remaining in the flow channel from the preceding measurement.

After a preceding measurement, in which a reaction front propagated exclusively in a first partial area of the reaction chamber, the reaction chamber is used in this way for an additional measurement, and the speed of the reaction front is detected in a second partial area of the reaction chamber. A plurality of measurements are performed in this way by means of a single reaction chamber.

It is possible for the user to select a mode of operation in which the measuring time and the flow rate or the speed of the reaction front are controlled or regulated such that a plurality of measurements are carried out with one reaction chamber. For example, the speed of the reaction front can be regulated such that a defined partial area of the reaction chamber, for example, the reaction front passes through, for example, one third of the reaction chamber.

While specific embodiments of the invention have been shown and described in detail to illustrate the application of the principles of the invention, it will be understood that the invention may be embodied otherwise without departing from such principles.

The invention claimed is:

1. A measuring device for measuring a concentration of gaseous and/or aerosol components of a gas mixture for a reaction carrier, which has at least one flow channel, wherein the flow channel forms a reaction chamber with a reactant and the reactant is designed to react with at least one component to be measured in the gas mixture or with a reaction product of the component to be measured in an optically detectable manner, the measuring device comprising:
 a detection unit having a lighting device for illuminating the reaction chamber of the reaction carrier, an optical sensor for detecting the optically detectable reaction, and an analysis unit for analyzing data of the optically detectable reaction, which data are provided by the optical sensor based on the detected reaction, and determination of a concentration of the component of the gas mixture; and
 a gas delivery unit having a gas delivery device for delivering the gas mixture through the gas outlet channel and a control/regulation unit, programmed to control or regulate a flow of the gas mixture through the flow channel as a function of at least one detected reaction rate parameter.

2. A measuring device in accordance with claim 1, wherein:
 the reaction rate parameter is a speed of a reaction front propagating in the direction of flow in the reaction chamber; and
 the detection unit is configured to detect the speed of the reaction front, and the control/regulation unit of the gas delivery unit is programmed to control or regulate the flow of the gas mixture through the flow channel as a function of the speed of the reaction front.

3. A measuring device in accordance with claim 1, wherein:

the reaction rate parameter is a temperature of the gas mixture flowing through the reaction chamber; and the detection unit is programmed to determine the temperature of the gas mixture, and the control/regulation unit of the gas delivery unit the flow of the gas mixture through the flow channel as a function of the temperature of the gas mixture.

4. A measuring device in accordance with claim 1, wherein the detection unit is programmed to detect an intensity gradient of a reaction front propagating in the direction of flow in the reaction chamber, and the analysis unit the concentration of the component to be measured in the gas mixture exclusively from optically detectable parameters.

5. A measuring system for measuring a concentration of gaseous and/or aerosol components of a gas mixture, the system comprising:
- a reaction carrier comprising:
  - at least one flow channel forming a reaction chamber with a reactant and the reactant is designed to react with at least one component to be measured in the gas mixture or with a reaction product of the component to be measured in an optically detectable manner; and
- a measuring device comprising:
  - a detection unit comprising a lighting device illuminating the reaction chamber of the reaction carrier, an optical sensor detecting the optically detectable reaction, an analysis unit for analyzing data of the optically detectable reaction, which data are provided by the optical sensor based on the detected reaction, and determining a concentration of the component of the gas mixture; and
  - a gas delivery unit comprising a gas delivery device delivering the gas mixture through the gas outlet channel and a control/regulation unit programmed to control or regulate a flow of the gas mixture through the flow channel as a function of a detected reaction rate parameter.

6. A measuring system in accordance with claim 5, wherein:
the reaction rate parameter is a speed of a reaction front propagating in the direction of flow in the reaction chamber;
the detection unit is programmed to detect the speed of the reaction front; and
the control/regulation unit of the gas delivery unit is configured to control or regulate the flow of the gas mixture through the flow channel as a function of the speed of the reaction front.

7. A measuring system in accordance with claim 5, wherein:
the reaction rate parameter is a temperature of the gas mixture flowing through the reaction chamber;
the detection unit is programmed to determine the temperature of the gas mixture; and
the control/regulation unit of the gas delivery unit is programmed to control or regulate the flow of the gas mixture through the flow channel as a function of the temperature of the gas mixture.

8. A measuring system in accordance with claim 5, wherein:
the detection unit is programmed to detect an intensity gradient of a reaction front propagating in the direction of flow in the reaction chamber, and the analysis unit is configured to determine the concentration of the component to be measured in the gas mixture exclusively from optically detectable parameters.

9. A measuring system according to claim 5, wherein the control/regulation unit and the analysis unit are part of a control unit, the control unit controlling:
illumination of the reaction chamber of the reaction carrier;
delivery of the gas mixture through the flow channel at a flow rate;
a detection of a reaction rate parameter during the delivery of the gas mixture;
the flow rate as a function of at least one reaction rate parameter; and
a determination of and an outputting of a measurement result of the concentration of the component of the gas mixture.

10. A measuring system in accordance with claim 9, wherein the control unit further controls:
detecting a temperature of the gas mixture flowing through the reaction chamber as a reaction rate parameter; and
the flow rate as a function of the temperature of the gas mixture.

11. A measuring system in accordance with claim 9, wherein the control unit further controls:
detecting a speed of a reaction front propagating in the direction of flow in the reaction chamber as a reaction rate parameter; and
the flow rate as a function of the speed of the reaction front.

12. A measuring system in accordance with claim 11, wherein the control unit further controls regulating the speed of the reaction front propagating in the direction of flow in the reaction chamber.

13. A measuring system in accordance with claim 11, wherein the control unit further controls delivery of the gas mixture at a maximum flow rate at the start of the delivery of the gas mixture through the flow channel.

14. A measuring system in accordance with claim 9, wherein the control unit further controls:
detecting an intensity gradient of a reaction front propagating in the direction of flow in the reaction chamber; and
determining the concentration of the component to be measured in the gas mixture exclusively from optically detectable parameters.

15. A measuring device for measuring a concentration of a gas mixture in a reaction chamber, the measuring device comprising:
a gas delivery device flowing the gas mixture through the reaction chamber;
a lighting device illuminating the reaction chamber;
a sensor detecting a reaction in the reaction chamber and generating a sensor signal representing a parameter of the reaction;
an analysis unit analyzing the sensor signal to determine the concentration of the gas mixture;
a control unit connected to said gas delivery device and programmed to control a flow of the gas mixture through the flow channel as a function of a detected parameter of the reaction in the reaction chamber.

16. A measuring system in accordance with claim 15, wherein:
said control unit is connected to said analysis unit;
the detected parameter is detected by said sensor.

17. A measuring system in accordance with claim 15, further comprising:

another sensor connected to said control unit and detecting the detected parameter.

\* \* \* \* \*